(12) United States Patent
Powell et al.

(10) Patent No.: US 12,239,462 B2
(45) Date of Patent: Mar. 4, 2025

(54) THERMALLY ACTUATED ELECTRODES FOR IMPROVED SKIN-CONTACT PHYSIOLOGICAL MEASUREMENTS

(71) Applicant: Apple Inc., Cupertino, CA (US)

(72) Inventors: Victoria M. Powell, San Francisco, CA (US); Ali Moin, San Mateo, CA (US)

(73) Assignee: Apple Inc., Cupertino, CA (US)

( * ) Notice: Subject to any disclaimer, the term of this patent is extended or adjusted under 35 U.S.C. 154(b) by 609 days.

(21) Appl. No.: 17/358,644

(22) Filed: Jun. 25, 2021

(65) Prior Publication Data

US 2022/0409137 A1    Dec. 29, 2022

(51) Int. Cl.
| | |
|---|---|
| *A61B 5/251* | (2021.01) |
| *A61B 5/00* | (2006.01) |
| *A61B 5/0531* | (2021.01) |
| *A61B 5/256* | (2021.01) |
| *A61B 5/28* | (2021.01) |
| *A61B 5/291* | (2021.01) |
| *A61B 5/296* | (2021.01) |

(52) U.S. Cl.
CPC .......... *A61B 5/6843* (2013.01); *A61B 5/0531* (2013.01); *A61B 5/251* (2021.01); *A61B 5/256* (2021.01); *A61B 5/28* (2021.01); *A61B 5/291* (2021.01); *A61B 5/296* (2021.01); *A61B 5/6844* (2013.01); *A61B 2562/0209* (2013.01)

(58) Field of Classification Search
CPC ..... A61B 5/6843; A61B 5/0531; A61B 5/251; A61B 5/256; A61B 5/28; A61B 5/291; A61B 5/296; A61B 2562/0209; A61B 5/6844
See application file for complete search history.

(56) References Cited

U.S. PATENT DOCUMENTS

| | | | | |
|---|---|---|---|---|
| 2012/0310067 | A1* | 12/2012 | Najafi | A61B 5/685 607/116 |
| 2017/0095670 | A1* | 4/2017 | Ghaffari | A61M 21/02 |
| 2017/0112438 | A1 | 4/2017 | Min et al. | |
| 2018/0345006 | A1 | 12/2018 | Ambrose | |
| 2020/0408615 | A1* | 12/2020 | Scott | G01L 1/02 |

FOREIGN PATENT DOCUMENTS

| | | |
|---|---|---|
| CN | 108778395 A | 11/2018 |
| JP | 2012-120705 A | 6/2012 |

OTHER PUBLICATIONS

"Nitinol / flexinol® actuator wire," Imagesco.com, May 1, 2001. [Online]. Available: https://www.imagesco.com/articles/nitinol/04.html. (Year: 2001).*

(Continued)

*Primary Examiner* — Joanne M Rodden
*Assistant Examiner* — Dana Stumpfoll
(74) *Attorney, Agent, or Firm* — BAKERHOSTETLER

(57) ABSTRACT

A device for skin-contact biological measurement includes one or more electrodes to enable signal transmission through a skin contact and a control mechanism coupled to the one or more electrodes to adjust an electrode-to-skin impedance (ESI). The control mechanism is configured to implement the ESI adjustment using a thermal actuator.

22 Claims, 5 Drawing Sheets

(56) References Cited

OTHER PUBLICATIONS

Archive.org. [Online]. Available: https://web.archive.org/web/20010501044624/https://www.imagesco.com/articles/nitinol/04.html. (Year: 2001).*
Wikipedia contributors, "First law of thermodynamics," Wikipedia, The Free Encyclopedia, Feb. 2, 2024. [Online]. Available: https://en.wikipedia.org/w/index.php?title=First_law_of_thermodynamics&oldid=1202114039. (Year: 2024).*
Potekhina, et al., "Review of Electrothermal Actuators and Applications," Actuators, vol. 8, No. 4, Sep. 21, 2019.
European Office Action from European Patent Application No. 22177773.3, dated Oct. 17, 2022, 6 pages.
Japanese Office Action from Japanese Patent Application No. 2022-093059, dated Jun. 19, 2023, 9 pages including machine-generated English language translation.
Japanese Office Action from Japanese Patent Application No. 2022-093059, dated Nov. 27, 2023, 8 pages including English language translation.
Japanese Notice of Allowance from Japanese Patent Application No. 2022-093059, dated May 27, 2024, 5 pages including machine-generated English language translation.
European Patent Application No. 22177773.3; Office Action dated Dec. 4, 2024, 8 pages.
Korean Office Action from Korean Patent Application No. 10-2022-0071955, dated Oct. 25, 2024, 13 pages with English translation.

* cited by examiner

THERMALLY ACTUATED ELECTRODES FOR IMPROVED SKIN-CONTACT PHYSIOLOGICAL MEASUREMENTS

TECHNICAL FIELD

The present description relates generally to sensor technology and, more particularly, to thermally actuated electrodes for improved skin-contact physiological measurements.

BACKGROUND

Physiological parameters are commonly measured using electronic devices with analog or digital displays that utilize skin-contact electrodes to provide detectable electrical signals. The electrodes are made of a conductive material such as a metal. Examples of biological measurements that rely on contact electrodes are electromyography (EMG), electrooculography (EOG), electroencephalogram (EEG), electrocardiogram (ECG), body temperature, blood pressure, heart rate measurement and the like. In a skin-contact physiological measurement, the quality of the skin contact can significantly affect the accuracy of the results. Currently, in some skin-contact physiological measurements, an electric conductive gel is applied to the electrode to control the impedance between the skin and the electrode, also known as the skin-electrode contact impedance. The contact impedance may be modeled with electrical elements such as a capacitor and one or more resistors.

BRIEF DESCRIPTION OF THE DRAWINGS

Certain features of the subject technology are set forth in the appended claims. However, for the purposes of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in a block diagram form in order to avoid obscuring the concepts of the subject technology.

The subject technology is generally directed to a device for skin-contact biological measurement. In some implementations, the disclosed device includes one or more electrodes to enable signal transmission through a skin contact and a control mechanism that is coupled to the electrodes to adjust an electrode-to-skin impedance (ESI). The control mechanism can apply electrical activation to implement the ESI adjustment, as discussed below.

In one or more implementations, an apparatus of the subject technology includes a processor and one or more electrodes mounted on a device and coupled to a control mechanism. The control mechanism is activatable by the processor and is able to adjust the ESI by maintaining a desired electrode-to-skin pressure with a varied contour of a local skin surface.

In some implementations, a system according to the subject technology includes a portable communication device and a device communicatively coupled to the portable communication device. The device includes one or more electrodes and a control mechanism coupled to the one or more electrodes to adjust the ESI by using a thermal actuator to maintain a desired electrode-to-skin pressure with a varied contour of users skin surface. In some aspects, the thermal actuator can convert thermal energy into mechanical energy via thermal expansion and contraction of solid material. Examples of thermal actuator include shape memory alloy (SMA) actuators, hot-and-cold-arm actuators, and bimorph type actuators. The shape memory alloys can, for example, be made of a nickel-titanium alloy. The hot-and-cold-arm actuators are based on the asymmetric thermal expansion in the micro-structure of a material. The bimorph type actuators may consist of two or more layers of dissimilar materials and operate based on the difference in the coefficient of thermal expansion (CTE) of the dissimilar materials.

Figure 1A:
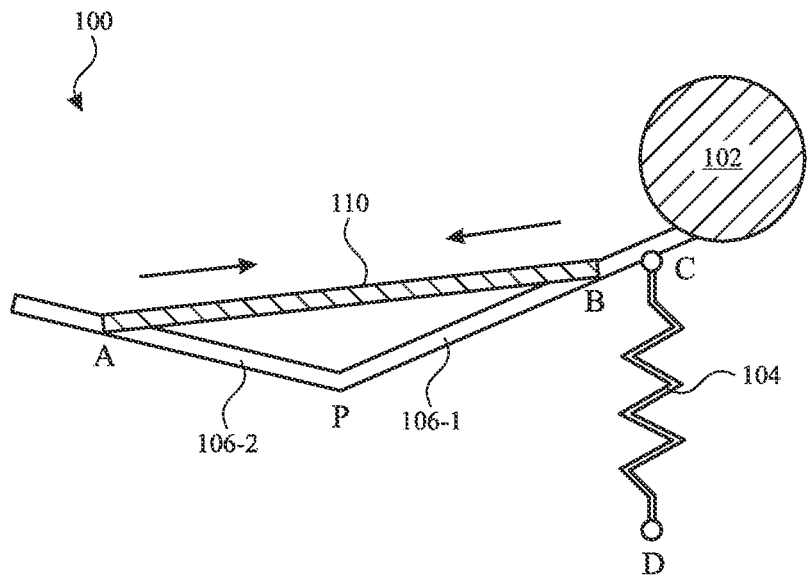
FIGS. 1A and 1B are diagrams illustrating a structure and operational states of an example of a device with an activated electrode for improved skin contact, in accordance with one or more aspects of the subject technology.
Figure 1B:
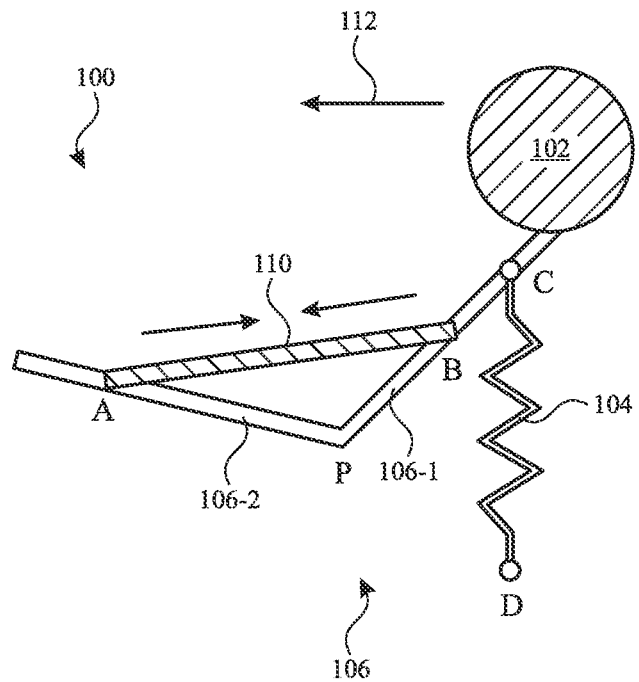

FIGS. 1A and 1B are diagrams illustrating a structure and operational states of an example of a device 100 with an activated electrode for improved skin contact, in accordance with one or more aspects of the subject technology. The device 100, as shown in FIG. 1A, includes an electrode 102, a spring 104, two rigid bars 106 (106-1 and 106-2) coupled together via a pivot P, and a thermal actuator 110 (hereinafter, actuator 110). The actuator 110 is coupled to the rigid bars 106 at points A and B, and the spring 104 is coupled to the rigid bar 106-1 at a point C and to a fixed location D. The length of the actuator 110 can be changed with the application of heat. The change in the length of the actuator 110 can cause movement of the electrode 102. For example, contraction of the actuator 110, as shown in FIG. 1B, can pull the electrode 102 in the direction of axis 112. This can maintain a desired pressure between the electrode 102 and an adjacent surface, such as a skin surface when the electrode 102 is part of a biological measurement system.

Biological measurement such as measurement of electroencephalogram (EEG) is an area of growing interest in wearable technology spaces. To take measurements using dry electrodes (without a conductive gel) presents multiple challenges that compromise the signal-to-noise ratio (SNR) of the reading. An important objective in these measurements is to reduce the ESI as much as possible. Good initial contact between the skin and the electrode is required for low ESI. In addition, the good electrode-to-skin contact should be maintained to avoid degradation of signal quality due to motion artifacts. According to some implementations of the subject technology, in the device 100 the actuator 110 can be realized using SMA or other actuators to increase electrode-to-skin contact force (or pressure). The increased contact force reduces initial ESI between the complex and varied skin contours that can be presented across the distribution of human population. Additionally, increased contact force allows for the contact to be maintained during the measurement due to increased retention of friction force. This also allows the electrode to be triggered when needed, avoiding high pressure points when measurements are not being taken. The SMA can be a nickel-titanium composite and acts like a contracting muscle when heated to its transition temperature. This material property of the SMA makes it an excellent candidate as a micro-actuator. The SMA actuator has advantageous features, for example, it is flexible (can be mounted on complex surfaces) and simple to use and has a low volume. Recent research results show that the addition of hafnium (hf) and Zirconium (Zr) can offer a broader transformation temperature range and greater dimension stability to the SMA.

Figure 2A:
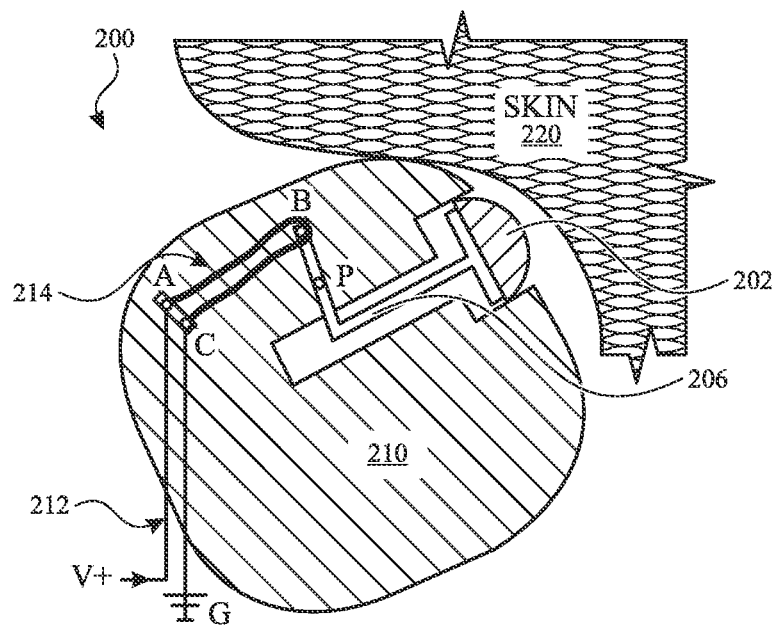
FIGS. 2A and 2B are diagrams illustrating a structure and operational states of an example of a device with an activated electrode for improved skin contact, in accordance with one or more aspects of the subject technology.
Figure 2B:
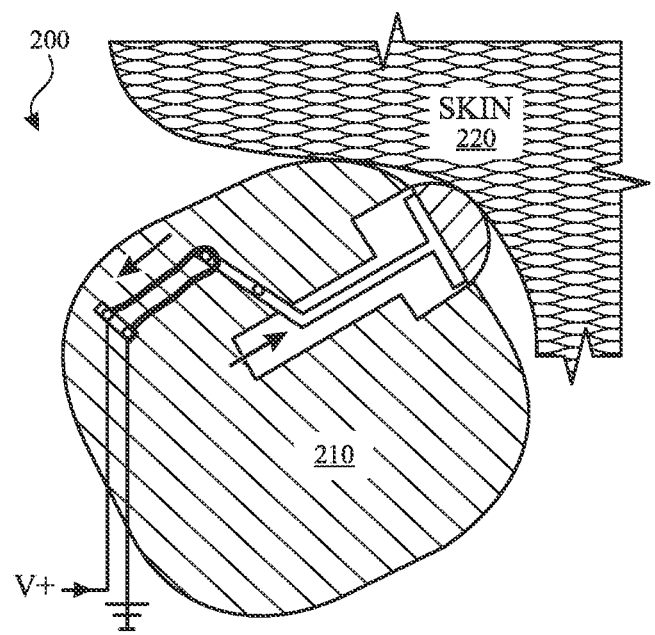

FIGS. 2A and 2B are diagrams illustrating a structure and operational states of an example of a device 200 with an activated electrode for improved skin contact, in accordance with one or more aspects of the subject technology. FIG. 2A shows the device 200 trying to be in contact with a skin 220. The device 200 has an activated electrode 202 coupled to a solid arm 206, which has a pivot P and is coupled to a thermal actuator 214 (hereinafter, actuator 214) at a point B. The actuator 214 is coupled, at points A and C, to wires 212 that connect the actuator 214 to a supply voltage V+ and ground potential G. The actuator 214 can be implemented using an SMA or other thermal expansion-contraction-based materials and is embedded into a support material 210 that forms part of the structure of the device 200. Examples of thermal actuator include hot-and-cold-arm actuators and bimorph type actuators, as explained above.

The supply voltage V+ can provide an electrical current that runs through the actuator 214 and causes contraction of the actuator 214, which results in insertion of a force to the solid arm 206 that in turn results in pushing the electrode 202 to the skin 220, as shown in FIG. 2B, in order to maintain a good electrode-to-skin contact.

Figure 3A:
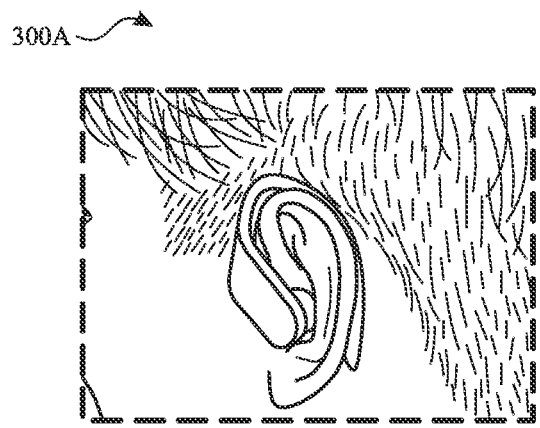
FIGS. 3A, 3B, 3C and 3D are diagrams illustrating example applications of an activated electrode for improved skin contact, in accordance with one or more aspects of the subject technology.

FIGS. 3A, 3B, 3C and 3D are diagrams illustrating example applications of an activated electrode for improved skin contact, in accordance with one or more aspects of the subject technology. FIG. 3A shows an around-the-ear headphone that can be used for EEG measurement by using the activated electrodes of the subject technology for improved skin contact.

Figure 3B:
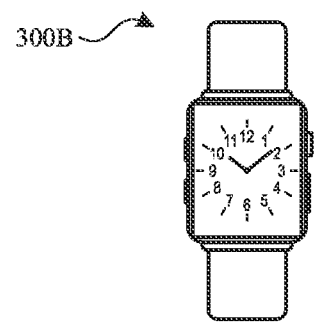

FIG. 3B shows a smartwatch that is enabled to make biological measurements such as blood pressure, heart rate and/or electrocardiogram (ECG) by contact electrodes, which can use the disclosed activated electrodes.

Figure 3C:
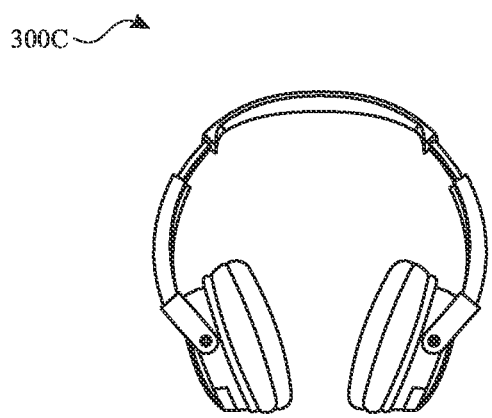

FIG. 3C shows an over-the-ear headphone that is enabled to make EEG measurement by using the disclosed activated electrodes of the subject technology.

Figure 3D:
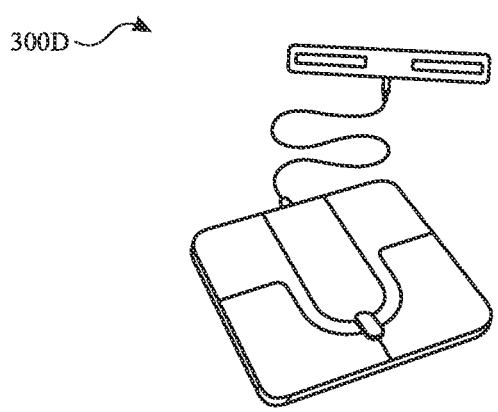

FIG. 3D shows a body-composition instrument such as a smart scale that is enabled to make one or more biological measurements by using the activated electrodes of the subject technology.

Figure 4A:
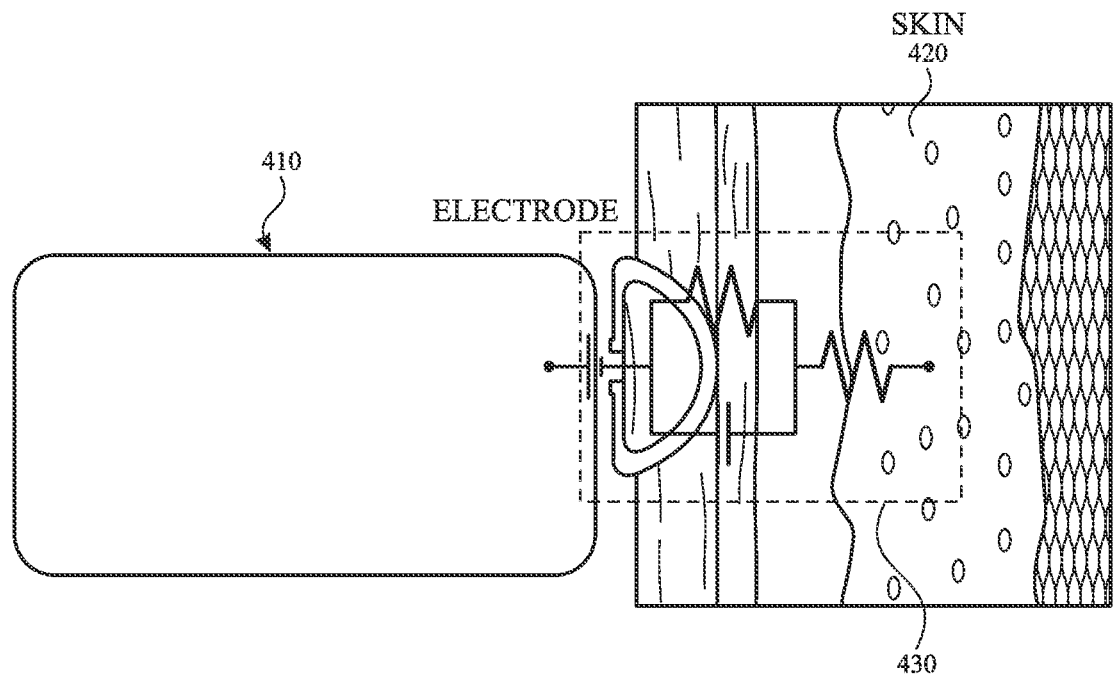
FIGS. 4A and 4B are diagrams illustrating an example of a device with an activated electrode for improved skin contact along with a corresponding electric circuit model, in accordance with one or more aspects of the subject technology.

FIG. 4A is a diagram illustrating an example of a device 410 with activated electrodes for improved skin contact along with a corresponding electric circuit model 430, in accordance with one or more aspects of the subject technology. The device 410 is shown in FIG. 4A to be in contact with skin 420. The device 410 can be structurally similar to the device shown in FIG. 3A with one or more activated electrodes of the subject technology. The electrode-to-skin contact has an ESI modeled with an electric circuit model 430.

Figure 4B:
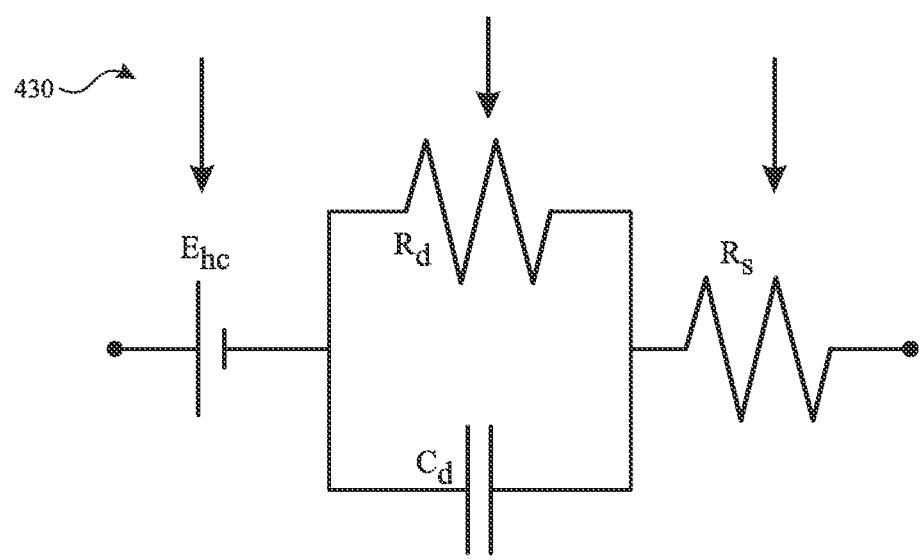

FIG. 4B shows the electric circuit model 430 that includes a resistance $R_s$ connected in series with a parallel-connected sub-circuit including a resistor ($R_d$) and a capacitor ($C_d$), which is connected to a half-cell potential difference ($E_{hc}$). The half-cell potential difference between the active electrode and a reference electrode should be minimized to reduce baseline drift and signal distortions. The active electrode is connected to a skin position receiving signals from the body, and the reference electrode is connected to a skin position covering a reference location on the body. The activated electrodes of the subject technology help to reduce the ESI and therefore improve the signal quality.

Figure 5:
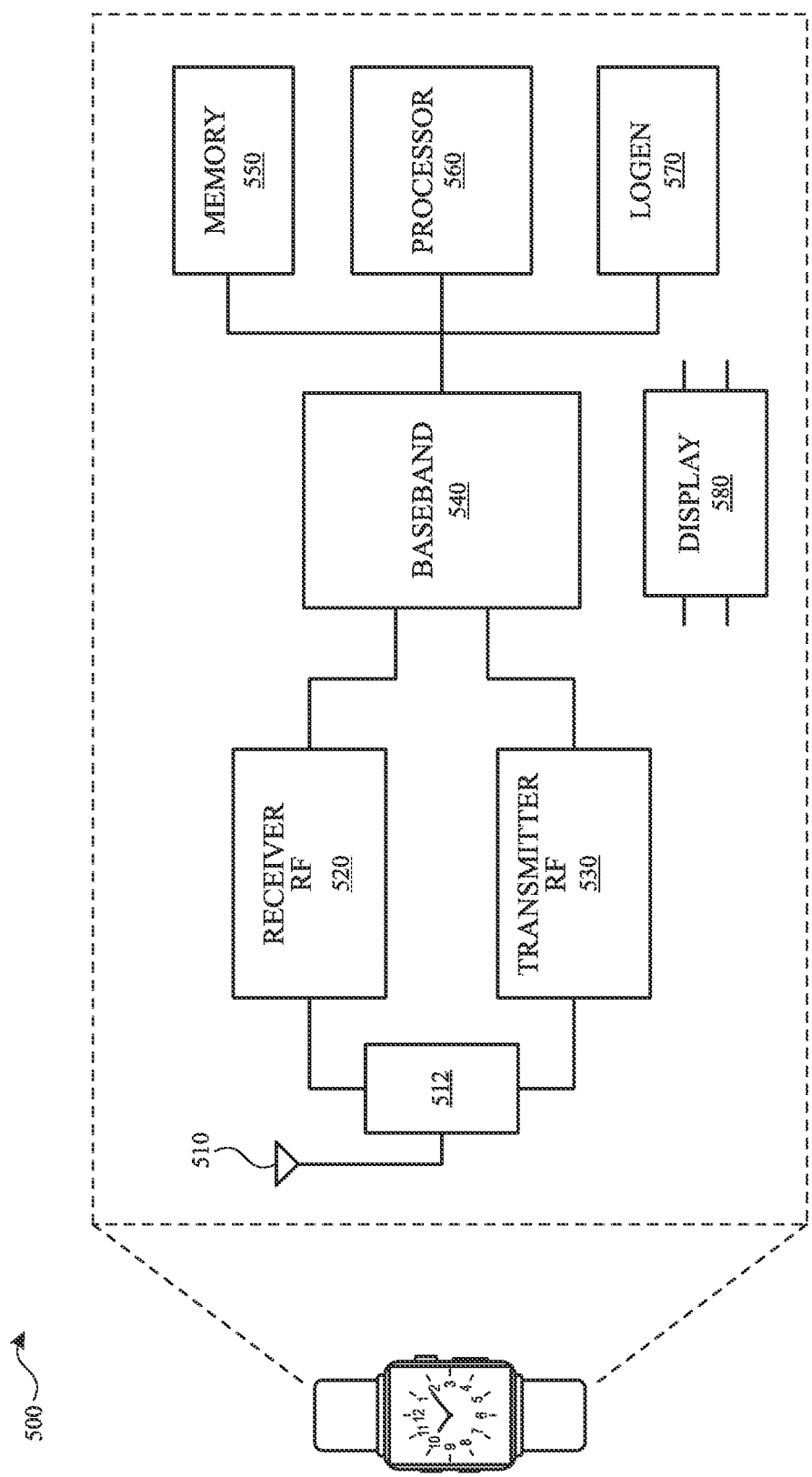
FIG. 5 is a block diagram illustrating a wireless communication device within which one or more aspects of the subject technology can be implemented.

FIG. 5 is a block diagram illustrating a wireless communication device 500 within which one or more aspects of the subject technology can be implemented. In one or more implementations, the wireless communication device 500 is a smartwatch that hosts a device of the subject technology including an activated electrode for improved skin contact. The wireless communication device 500 may comprise a radio-frequency (RF) antenna 510, a duplexer 512, a receiver 520, a transmitter 530, a baseband-processing module 540, a memory 550, a processor 560, a local oscillator generator (LOGEN) 570, and a display 580. In various embodiments of the subject technology, one or more of the blocks represented in FIG. 5 may be integrated on one or more semiconductor substrates. For example, the blocks 520-570 may be realized in a single chip or a single system on a chip, or may be realized in a multichip chipset.

The receiver 520 may comprise suitable logic circuitry and/or code that may be operable to receive and process signals from the RF antenna 510. The receiver 520 may, for example, be operable to amplify and/or down-convert received wireless signals. In various embodiments of the subject technology, the receiver 520 may be operable to cancel noise in received signals and may be linear over a wide range of frequencies. In this manner, the receiver 520 may be suitable for receiving signals in accordance with a variety of wireless standards, such as Wi-Fi, WiMAX, Bluetooth, and various cellular standards. In various embodiments of the subject technology, the receiver 520 may not use any saw-tooth acoustic wave (SAW) filters and few or no off-chip discrete components such as large capacitors and inductors.

The transmitter 530 may comprise suitable logic circuitry and/or code that may be operable to process and transmit signals from the RF antenna 510. The transmitter 530 may, for example, be operable to up-convert baseband signals to RF signals and amplify RF signals. In various embodiments of the subject technology, the transmitter 530 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 530 may be operable to provide signals for further amplification by one or more power amplifiers.

The duplexer 512 may provide isolation in the transmit band to avoid saturation of the receiver 520 or damaging parts of the receiver 520, and to relax one or more design requirements of the receiver 520. Furthermore, the duplexer 512 may attenuate the noise in the receive band. The duplexer 512 may be operable in multiple frequency bands of various wireless standards.

The baseband-processing module 540 may comprise suitable logic, circuitry, interfaces, and/or code that may be operable to perform processing of baseband signals. The baseband-processing module 540 may, for example, analyze received signals and generate control and/or feedback signals for configuring various components of the wireless communication device 500, such as the receiver 520. The baseband-processing module 540 may be operable to encode, decode, transcode, modulate, demodulate, encrypt, decrypt, scramble, descramble, and/or otherwise process data in accordance with one or more wireless standards.

The processor 560 may comprise suitable logic, circuitry, and/or code that may enable processing data and/or controlling operations of the wireless communication device 500. In this regard, the processor 560 may be enabled to provide control signals to various other portions of the wireless communication device 500. The processor 560 may also control the transfer of data between or among various portions of the wireless communication device 500. Additionally, the processor 560 may enable implementation of an operating system or otherwise execute code to manage the operations of the wireless communication device 500. In one or more implementations, the processor 560 can be used to control the operation of the control mechanisms by controlling the amount of current passing through the actuator (e.g., 214 of FIG. 2A). The processor 560 can further process the signals received from the electrodes (e.g., 202 of FIG. 2).

The memory 550 may comprise suitable logic, circuitry, and/or code that may enable storage of various types of information such as received data, generated data, code, and/or configuration information. The memory 550 may comprise, for example, RAM, ROM, flash, and/or magnetic storage. In various embodiments of the subject technology, information stored in the memory 550 may be utilized for configuring the receiver 520 and/or the baseband-processing module 540.

The LOGEN 570 may comprise suitable logic, circuitry, interfaces, and/or code that may be operable to generate one or more oscillating signals of one or more frequencies. The LOGEN 570 may be operable to generate digital and/or analog signals. In this manner, the LOGEN 570 may be operable to generate one or more clock signals and/or sinusoidal signals. Characteristics of the oscillating signals such as the frequency and duty cycle may be determined based on one or more control signals from, for example, the processor 560 and/or the baseband-processing module 540.

In operation, the processor 560 may configure the various components of the wireless communication device 500 based on a wireless standard according to which it is desired to receive signals. Wireless signals may be received via the RF antenna 510, amplified, and down-converted by the receiver 520. The baseband-processing module 540 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device, data to be stored to the memory 550, and/or information affecting and/or enabling operation of the wireless communication device 500. The baseband-processing module 540 may modulate, encode, and perform other processing on audio, video, and/or control signals to be transmitted by the transmitter 530 in accordance with various wireless standards.

In some aspects, the disclosed device includes one or more electrodes to enable signal transmission through a skin contact and a control mechanism that is coupled to the electrodes to adjust an ESI. The control mechanism can apply electrical activation to implement the ESI adjustment, as discussed below.

In some other aspects, an apparatus of the subject technology includes a processor and one or more electrodes mounted on a device and coupled to a control mechanism. The control mechanism is activatable by the processor and is able to adjust the ESI by maintaining a desired electrode-to-skin pressure with a varied contour of a local skin surface.

In yet other aspects, a system according to the subject technology includes a portable communication device and a device communicatively coupled to the portable communication device. The device includes one or more electrodes and a control mechanism coupled to the one or more electrodes to adjust the ESI by using a thermal actuator to maintain a desired electrode-to-skin pressure with a varied contour of a skin surface.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter genders (e.g., her and its) and vice versa. Headings and subheadings, if any, are used for convenience only and do not limit the subject disclosure.

The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. A phrase such as "an aspect" may refer to one or more aspects and vice versa. A phrase such as "a configuration" does not imply that such configuration is essential to the subject technology or that such configuration applies to all configurations of the subject technology. A disclosure relating to a configuration may apply to all configurations, or one or more configurations. A phrase such as "a configuration" may refer to one or more configurations and vice versa.

The word "example" is used herein to mean "serving as an example or illustration." Any aspect or design described herein as an "example" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims.

Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A device for skin-contact biological measurement, the device comprising:
   one or more electrodes configured to enable signal transmission through a skin contact; and
   a control mechanism comprising a plurality of rigid bars coupled to one another by a pivot and further coupled to the one or more electrodes and to a thermal actuator, wherein the control mechanism is configured to adjust an electrode-to-skin impedance (ESI) using the thermal actuator that causes the plurality of rigid bars to rotate about the pivot in opposite directions to cause movement in the one or more electrodes based on a change in length of the thermal actuator.

2. The device of claim 1, wherein the one or more electrodes comprise dry electrodes applicable to skin without an additional conductive medium.

3. The device of claim 2, wherein the one or more electrodes comprise bio-signal electrodes configured to be applicable to the skin without a conductive gel.

4. The device of claim 1, wherein the control mechanism comprises a spring coupled between at least one of the plurality of rigid bars and a fixed location to move the one or more electrodes back and forth between contractions of the thermal actuator.

5. The device of claim 1, wherein the thermal actuator comprises a thermal expansion-contraction-based actuator.

6. The device of claim 1, wherein the thermal actuator comprises a shape memory alloy, wherein the shape memory alloy comprises a nickel-titanium alloy.

7. The device of claim 1, wherein the thermal actuator comprises a hot-and-cold-arm actuator.

8. The device of claim 1, wherein the control mechanism is configured to achieve ESI adjustment by maintaining a desired electrode-to-skin pressure with a varied contour of a local skin surface.

9. The device of claim 1, wherein the one or more electrodes comprise electrocardiogram (ECG) electrodes configured to be applicable to the skin without a conductive gel.

10. The device of claim 1, wherein the control mechanism is configured to be activated by a processor during the skin-contact biological measurement.

11. The device of claim 1, wherein the thermal actuator causes rotational movement of each of the plurality of rigid bars about the pivot and further causes lateral movement of the one or more electrodes in a same direction as one of the plurality of rigid bars.

12. The device of claim 1, wherein the thermal actuator causes rotational movement of a first rigid bar of the plurality of rigid bars about the pivot in a first direction and further causes rotational movement of a second rigid bar of the plurality of rigid bars about the pivot in a second direction different from the first direction.

13. An apparatus comprising:
   a processor; and
   one or more electrodes mounted on a device and coupled to a control mechanism,
   wherein:
      the control mechanism is thermally actuated by the processor, and
      the control mechanism comprising a plurality of rigid bars coupled to one another by a pivot and further coupled to a thermal actuator, wherein the control mechanism is configured to adjust an ESI by using the thermal actuator for maintaining a desired electrode-to-skin pressure with a varied contour of a local skin surface, wherein the thermal actuator causes the plurality of rigid bars to rotate about the pivot in opposite directions to cause movement in the one or more electrodes based on a change in length of the thermal actuator.

14. The apparatus of claim 13, wherein the device comprises one of a smartwatch, a body-composition instrument, a head-mounted device or a wearable device with embedded electrodes.

15. The apparatus of claim 13, wherein the device is configured to perform a skin-contact biological measurement, wherein the skin-contact biological measurement comprises an EEG measurement, an electromyography (EMG) measurement or an ECG measurement without a need to apply a conductive gel to the one or more electrodes.

16. The apparatus of claim 13, wherein the processor is configured to activate the control mechanism during a skin-contact biological measurement.

17. The apparatus of claim 13, wherein the control mechanism further includes the thermal actuator.

18. The apparatus of claim 17, wherein the thermal actuator comprises a shape memory alloy, wherein the shape memory alloy comprises a nickel-titanium alloy.

19. A system comprising:
   a portable communication device; and
   a device communicatively coupled to the portable communication device,
   wherein:
      the device includes:
         one or more electrodes; and
         a control mechanism comprising a plurality of rigid bars coupled to one another by a pivot and further coupled to the one or more electrodes and to a thermal actuator, wherein the control mechanism is configured to adjust an ESI by using the thermal actuator to maintain a desired electrode-to-skin pressure with a varied contour of a skin surface, wherein the thermal actuator causes the plurality of rigid bars to rotate about the pivot in opposite directions to cause movement in the one or more electrodes based on a change in length of the thermal actuator.

20. The system of claim 19, wherein the thermal actuator comprises a thermal expansion-contraction-based actuator.

21. The system of claim 19, wherein the one or more electrodes comprise dry electrodes applicable to skin without an additional conductive medium.

22. The system of claim 19, wherein the thermal actuator comprises a shape memory alloy, and wherein the shape memory alloy comprises a nickel-titanium alloy.

* * * * *